(12) United States Patent
Chen

(10) Patent No.: US 12,290,534 B2
(45) Date of Patent: May 6, 2025

(54) PAIN RELIEF COMPOSITION AND METHOD OF USE

(71) Applicant: Cheng Chen, Regina (CA)

(72) Inventor: Cheng Chen, Regina (CA)

( * ) Notice: Subject to any disclaimer, the term of this patent is extended or adjusted under 35 U.S.C. 154(b) by 289 days.

(21) Appl. No.: 17/732,015

(22) Filed: Apr. 28, 2022

(65) Prior Publication Data

US 2023/0346840 A1 Nov. 2, 2023

(51) Int. Cl.
*A61K 35/20* (2006.01)
*A61K 9/06* (2006.01)
*A61K 31/07* (2006.01)
*A61K 31/23* (2006.01)

(52) U.S. Cl.
CPC ............... *A61K 35/20* (2013.01); *A61K 9/06* (2013.01); *A61K 31/07* (2013.01); *A61K 31/23* (2013.01)

(58) Field of Classification Search
CPC .......... A61K 35/20; A61K 9/06; A61K 31/07; A61K 31/23
USPC ........................................................ 424/535
See application file for complete search history.

(56) References Cited

U.S. PATENT DOCUMENTS

2008/0286416 A1 * 11/2008 Euber .................... A23L 33/40
  426/580
2017/0042801 A1 * 2/2017 Medri .................... A61K 8/678

FOREIGN PATENT DOCUMENTS

WO    WO 2020/188305    *  9/2020

* cited by examiner

*Primary Examiner* — Jennifer M. H. Tichy
(74) *Attorney, Agent, or Firm* — David W. Barman

(57) ABSTRACT

The present invention the novel ointment composition based on milkfat obtained from human breast milk and combined with a synergistically beneficial ratio of medium chain triglycerides to milk fat from human breast milk.

2 Claims, No Drawings

PAIN RELIEF COMPOSITION AND METHOD OF USE

BACKGROUND OF THE INVENTION

There is an ever-growing need for effective topical analgesic and pain relief compositions. One significant area of concern related to side effects when using most conventional topical pain relief products. Although the marketplace is replete with pharmaceutical and natural remedies for topical use, there still remains a concern relating to efficacy and undesired side effects.

The present invention addresses this issue.

SUMMARY OF THE INVENTION

The present invention has presently discovered a topical pain relief composition based primarily on an ointment in which the base is formed of human breast milk.

In one embodiment, the invention is analgesic ointment composition comprising:
milk fat from human breast milk;
medium chain triglycerides (MCT) derived from organic modified coconut oil, whereby the milk fat from human breast milk and MCT are present in a synergetic ratio of milk fat from human breast milk:MCT of 1:2.638-67.919; and Vitamin A all trans palmitate 10,000-30,000 IU.

In one embodiment, the synergetic ratio is
milk fat from human breast milk:MCT of 1:1.516-4.553.

In one embodiment, the method of making an ointment composition of claim 1, said method comprising the steps of:
providing 230-240 ml of human breast milk; placing said human breast milk in a container;
placing the human breast milk container in a second container filled with water in a double boiler configuration;
heating using a heat source, said human breast milk to 60° C.;
maintaining said heating for 30-40 minutes starting from time said heating step reaches a minimum of 60° C.;
adding 0.033-0.099 ml of Vitamin A all trans palmitate solution having 10,000-30,000 IU Vitamin A subsequent to said 30-40 minutes of maintaining said heating;
adding 0.017-0.051 ml Medium Chain Triglycerides (MCT) is derived from organic modified coconut oil;
stirring said composition gently as to minimize ambient air introduced to said composition;
removing said composition from a heat source cooling said composition from said heat source and allowing said composition to cool to room temperature of 20-25° C.;
maintaining said composition at said room temperature 3-4 hours, during said maintaining, an oil phase will form, separate, and rise to an upper portion of said container; removing said oil phase;
cooling said oil phase 3-4 hours at 1-3° C.

As generally understood, commonly used, and used herein, a double boiler configuration is when a smaller container is placed within a larger container and the larger container is filled with liquid. The large container containing the smaller container is placed on a heat source. In the present invention, the temperature of both the larger container containing water and the smaller container containing breast milk is monitored to make sure the breast milk is maintained at or around 60° C.

In one embodiment, the invention is analgesic ointment composition consisting of:
milk fat from human breast milk; medium chain triglycerides (MCT) derived from organic modified coconut oil, whereby the milk fat from human breast milk and MCT are present in a synergetic ratio of milk fat from human breast milk:MCT of 1:2.638-67.919; and
Vitamin A all trans palmitate 10,000-30,000 IU.

In one embodiment, the synergetic ratio is
milk fat from human breast milk:MCT of 1:1.516-4.553.

In one embodiment, the method of making an ointment composition as disclosed herein, said method consisting of the steps of:
providing 230-240 ml of human breast milk;
placing said human breast milk in a container;
placing the human breast milk container in a second container filled with water in a double boiler configuration;
heating using a heat source, said human breast milk to 60° C.; maintaining said heating for 30-40 minutes starting from time said heating step reaches a 60° C.;
adding 0.033-0.099 ml of Vitamin A all trans palmitate solution having 10,000-30,000 IU Vitamin A subsequent to said 30-40 minutes of maintaining said heating;
adding 0.017-0.051 ml Medium Chain Triglycerides (MCT) is derived from organic modified coconut oil;
stirring said composition gently as to minimize ambient air introduced to said composition;
removing said composition from a heat source cooling said composition from said heat source and allowing said composition to cool to room temperature of 20-25° C.;
maintaining said composition at said room temperature 3-4 hours, during said maintaining, an oil phase will form, separate, and rise to an upper portion of said container; removing said oil phase;
cooling said oil phase 3-4 hours at 1-3° C.

DETAILED DESCRIPTION OF THE PREFERRED EMBODIMENTS

The present invention is an analgesic ointment.

Raw human breast milk is utilized. The breast milk is either fresh or frozen.

Raw breast milk, 230-240 ml is heated to 60° C. and held at this temperature for 30-40 min. Human breastmilk is known to comprise 3 to 5% milk fat. This would provide between 6.9 and 12 g milk fat to the composition.

At the end of the heating, and while maintaining the temperature, 0.033-0.099 of Vitamin A, all trans palmitate, is added. This addition is 10,000-30,000 IU of Vitamin A.

Subsequent to the Vitamin A addition, is the addition of Medium Chain Triglycerides (MCT). As used herein, the MCT is derived from organic modified coconut oil. The MCT is added in 0.017-0.051 ml.

The mixture is stirred gently for 45-60 seconds. Gentle stirring, as generally understood, is circular stilling in which minimal ambient air is introduced to the mixture.

The mixture is then removed from the heat source and permitted to cool to room temperature, 20-25° C. and remain undisturbed rest over a time period of four hours.

During the resting time, the oil phase of the breast milk containing the added Vitamin A and MCT will rise to the top of the container.

At the end of four hours, the oil phase is skimmed from the top portion of the mixture. The oil phase is then placed in a refrigerator set at 1-3° C. The skimmed oil phase remains at 1-3° C. a minimum of four hours. During this time, the oil phase will increase in viscosity and have the consistency of an ointment. As generally understood, topical ointments have a viscosity a standard temperature and pressure between 1000-12000 cP.

The resulting product has a novel synergistic ratio of
Human Milk Fat:MCT Fat
1:2.638-67.919.

In one embodiment, the synergistic ratio of Human Milk Fat:MCT Fat is:
1:1.516-4.553

This ratio is combined with 10,000-30,000 IU of Vitamin A as disclosed above.

The composition as described herein has been observed to be stable for 7 to 10 days when the composition is stored refrigerated at a temperature between 1-3° C.

In use, a user will apply a topical film to an area of the skin in need of analgesic therapy. The film is applied one to three times a day for up to seven days.

In another method of use, ointment is applied every 2-3 hours with no maximum daily usage limit.

While the invention has been described in its preferred form or embodiment with some degree of particularity, it is understood that this description has been given only by way of example and that numerous changes in the details of construction, fabrication, and use, including the combination and arrangement of parts, may be made without departing from the spirit and scope of the invention.

What is claimed:

1. A method of making an analgesic ointment composition, said method comprising steps of:

providing 230-240 ml of human breast milk;

placing said human breast milk in a container;

placing said human breast milk container in a second container filled with water in a double boiler configuration;

heating, using a heat source, said human breast milk to 60° C.;

maintaining said heating for 30-40 minutes starting from time said heating step reaches a minimum of 60° C.;

adding 0.033-0.099 ml of Vitamin A palmitate solution having 10,000-30,000 IU Vitamin A subsequent to said 30-40 minutes of maintaining said heating;

adding 0.017-0.051 ml Medium Chain Triglycerides (MCT) derived from organic modified coconut oil, said adding resulting in a synergetic ratio of milk fat from human breast milk:MCT of 1:2.638-67.919;

stirring said composition gently as to minimize ambient air introduced to said composition;

removing said composition from said heat source and allowing said composition to cool to room temperature of 20-25° C.;

maintaining said composition at said room temperature 3-4 hours to form an oil phase, said oil phase separating and rising to an upper portion of said human breast milk container;

removing said oil phase; and cooling said oil phase 3-4 hours at 1-3° C.

2. The method of claim 1, wherein said adding 0.017-0.051 ml Medium Chain Triglycerides (MCT) results in said composition having a synergetic ratio of milk fat from human breast milk:MCT of 1:1.516-4.553.

* * * * *